United States Patent [19]

Samsel

[11] Patent Number: 5,210,338
[45] Date of Patent: May 11, 1993

[54] CATALYZED CHAIN GROWTH PROCESS

[75] Inventor: Edward G. Samsel, Baton Rouge, La.

[73] Assignee: Ethyl Corporation, Richmond, Va.

[21] Appl. No.: 881,928

[22] Filed: May 12, 1992

Related U.S. Application Data

[63] Continuation-in-part of Ser. No. 782,116, Oct. 25, 1991, abandoned.

[51] Int. Cl.$^5$ .......... C07C 29/54; C07C 2/88; C07C 31/125; C07F 5/06
[52] U.S. Cl. .......... 568/911; 556/190; 585/637
[58] Field of Search .......... 556/190; 568/911; 585/637

[56] References Cited

U.S. PATENT DOCUMENTS

| | | | |
|---|---|---|---|
| 2,977,381 | 3/1961 | Roha et al. | 568/911 |
| 3,017,438 | 1/1962 | Atwood | 568/911 |
| 3,376,331 | 4/1968 | Kroll | 556/190 |
| 3,415,861 | 12/1968 | Davis et al. | 568/911 |
| 3,476,788 | 11/1969 | Bruno | 556/190 |
| 3,476,789 | 11/1969 | Bruno | 556/190 |
| 3,551,467 | 12/1970 | Arakawa et al. | 556/190 |
| 4,268,697 | 5/1981 | Gibson | 568/911 |
| 4,851,378 | 7/1989 | Malpass et al. | 556/190 |

*Primary Examiner*—Joseph E. Evans
*Attorney, Agent, or Firm*—David M. Bunnell

[57] ABSTRACT

An improved process for the preparation of higher aluminum alkyls by a chain growth reaction of an α-olefin and especially ethylene with a lower molecular weight aluminum alkyl or aluminum hydride uses a catalyst system which comprises at least one of (a) a metallocene of a transition metal and an aluminoxane (b) a cationic transition metal metallocene complex with an inert, non-coordinating anion, and (c) a cationic transition metal metallocene complex with an inert, non-coordinating anion and a hydrocarbylaluminoxane. Higher purity alpha olefins can be recovered by olefin displacement. Alternatively, linear primary alcohols can be produced by oxidation and hydrolysis.

26 Claims, No Drawings

CATALYZED CHAIN GROWTH PROCESS

This application is a continuation-in-part of pending application Ser. No. 07/782,116, filed Oct. 25, 1991, now abandoned whose entire teachings are hereby incorporated by reference.

This invention relates generally to the preparation of aluminum alkyls by the chain growth reaction of a lower olefin, especially ethylene, with a lower molecular weight alkyl aluminum and more specifically to an improved chain growth process using a catalyst system which includes a combination of a metallocene of a transition metal and a hydrocarbylaluminoxane, and/or a cationic transition metal metallocene complex containing inert, non-coordinating anions, either alone or in combination with a hydrocarbylaluminoxane, to catalyze said reaction.

Alpha-olefins and alcohols are made in commercial quantities by a process initially developed in the fifties by Karl Ziegler and his co-workers. The so-called Ziegler process typically involves the reaction of triethyl aluminum ("TEA") and ethylene in an α-olefin solvent at temperatures in the range of 100°–200° C. and pressures in the range of 2000–4000 psig to yield a mixture of $C_{2-20}$ olefins and tri-$C_{2-20+}$ alkyl aluminums having a Poisson alkyl distribution. Alpha-olefins are recovered from the aluminum alkyls by olefin displacement using, for example, ethylene. Alternatively, linear primary higher alcohols are produced from the aluminum alkyls by oxidation and hydrolysis.

The alpha-olefins contain internal and vinylidene olefin impurities which, because they boil very close to the alpha-olefins of similar carbon number, are difficult to remove by distillation. The purities of the alpha-olefins typically produced for the different carbon numbers are as follows:

|          | $C_6$ | $C_8$ | $C_{10}$ | $C_{12}$ | $C_{12-14}$ | $C_{14-16}$ | $C_{16-18}$ |
|----------|------|------|------|------|------|------|------|
| wt. % α-olefin | 97.5 | 96.5 | 96.2 | 93.5 | 87.0 | 76.9 | 62.7 |

In some cases the vinylidene olefin content of the olefin mixtures is not detrimental. It is known that vinylidene olefins are readily sulfonated but the detergency and wetting performance of the derived sulfonates are inferior to those of sulfonates based on the corresponding linear α-olefins. Similar reservations apply to sulfonates of internal olefins. Also, as is well known, the reaction of α-olefins with HBr can lead to the 1-bromo or to the 2-bromo derivative depending on the reaction conditions. In the detergent industry, the 1-bromo derivatives are of more interest as they provide a route to alkyldimethylamines and dialkylmethylamines which are converted to amine oxides and to quaternary amines. It is reported that any internal olefins present will react to form internal bromides. Similarly, vinylidene olefins could rapidly add HBr to give tertiary alkylbromides. Hence, an α- olefin which contains isomeric olefins would lead ultimately to a tertiary amine containing an undesirable range of isomeric tertiary amines.

The chain growth process has now been improved by using a catalyst which permits the process to be efficiently carried out at milder temperatures and pressures. This results in a less hazardous process giving more linear products at lower energy cost. The new process gives an oligomer chain length distribution described by the Schulz-Flory distribution, except at high conversion.

In accordance with this invention there is provided an improved process for the preparation of an aluminum alkyl chain growth product by the chain growth reaction of α-olefin on an aluminum alkyl, the improvement comprising catalyzing the chain growth reaction with a catalyst system which comprises at least one of the following: (a) a metallocene of a transition metal and a methylaluminoxane, (b) a cationic transition metal metallocene complex with an inert non-coordinating anion, and (c) a cationic transition metal metallocene complex with an inert, non-coordinating anion and a hydrocarbylaluminoxane.

Also provided is an improved process for the preparation of linear alpha-olefins by the chain growth reaction of α-olefin on an aluminum alkyl followed by olefin displacement of linear alpha-olefins from the aluminum alkyl chain growth product, the improvement comprising catalyzing the chain growth reaction with a catalyst system which comprises at least one of the following: (a) a metallocene of a transition metal and a methylaluminoxane, (b) a cationic transition metal metallocene complex with an inert, non-coordinating anion and, (c) a cationic transition metal metallocene complex with an inert, non-coordinating anion and a hydrocarbylaluminoxane.

Also provided is an improved process for the preparation of linear primary alcohols by the chain growth reaction of α-olefin on an aluminum alkyl followed by oxidation of the aluminum alkyl chain growth product to form alkoxides and acid hydrolysis of the alkoxides to produce linear primary alcohols, the improvement comprising catalyzing the chain growth reaction with a catalyst system which comprises at least one of the following: (a) a metallocene of a transition metal and a methylaluminoxane (b) a cationic transition metal metallocene complex with an inert, non-coordinating anion and, (c) a cationic transition metal metallocene complex with an inert, non-coordinating anion and a hydrocarbylaluminoxane.

Examples of α-olefins suitable for chain growth include, but are not limited to, $C_2$ to $C_6$ straight chain α-olefins with ethylene being the preferred olefin. The growth of alkyl chains on aluminum alkyls in accordance with the process of the invention is catalyzed by metallocene derivatives of Group 3, 4 and 5 metals (Periodic Table as recently set forth by the IUPAC and ACS nomenclature committees) and preferably Ti, Zr, Hf, Sc, Y, Nb and Ta.

Suitable transition metal metallocene catalyst systems for use in the process of the invention include:

(A) an uncharged transition metal metallocene and methylaluminoxane.

(B) a cationic transition metal metallocene complex with a hydrocarbyl ligand or hydride containing an inert, non-coordinating anion, and (C) a cationic transition metal metallocene complex with a hydrocarbyl ligand or hydride containing an inert, non-coordinating anion, and a hydrocarbylaluminoxane.

In equation 1 below for a typical ethylene chain growth process according to the invention, R represents H and/or a $C_1$ to $C_8$ alkyl chain. The R groups may be mixed on Al or a homoleptic trialkyl aluminum may be used. The subscript x, here called the conversion or R groups in $R_3Al$, is in the range $x=0-3$. The length of the alkyl chains essentially follow the Schulz- Flory distribution, at least at $x \lesssim 2$. This statistical distribution is described by: $X_p = \beta/(1+\beta)^p$, where $X_p$ is the mole fraction at a chain length set by p, p is the number of added ethylenes and $\beta$ is the Schulz-Flory distribution coefficient. In this invention, polyethylene (PE) is frequently formed as a co-product unrelated to the Schulz-Flory distribution.

$$R_3Al + xpC_2H_4 \xrightarrow{Cat} [R(CH_2CH_2)_p]_xAlR_{(3-x)} \qquad 1.$$

The primary catalyst can be a $d^0$ organometallic compound of a transition metal such as titanium, preferably zirconium or more preferably hafnium. As used in this application the term "metallocene" includes metal derivatives which contain at least one cyclopentadienyl moiety. The catalyst structure may be described as metallocene (or bent metallocene in the case of bis-cyclopentadienyl compounds) with ancillary anionic ligands or hydrocarbyl groups, such as metallocenes of the formula $Z_t (\eta^5 - R'_nH_mC_5)_sMX_{4-s}$, where R' is a carbon or a carbon and heteroatom (N, O, S, P, B, Si and the like) containing $C_1$ to $C_6$ alkyl, $C_3$ to $C_{13}$ cycloalkyl or a $C_6$ to $C_{14}$ aryl group. Non-limiting examples of such groups include methyl, ethyl, trimethylsilyl, t-butyl, cyclohexyl, phenyl, 4-methylphenyl, 2,4,6-trimethylphenyl and the like. The R' substituents can be different in type and number on each cyclopentadienyl ring and can form fused cyclic groups attached to the ring. Z is a bridging group between two cyclopentadienyl rings such as silane, phosphine, amine or carbon groups, t is 0 or 1, m and n are integers of 0 to 5, $m+n = 5$ when t is 0 and 4 when t is 1, s is 1 or 2, M is the transition metal and X is halogen, psuedohalogen, (e.g. a leaving group in nucleophilic substitution such as ester, cyanide, tosylate, triflate, $\beta$-diketonate and the like), hydride or $C_1$ to $C_8$ alkyl. Analogous metallocenes with two different X groups are also effective in the presence of an aluminoxane. Also effective are bimetallic $\mu$-oxo analogues such as $O[ClHf(C_5H_5)_2]_2$ and monocyclopentadienyl metal trihalides.

Another useful form of the primary catalyst is a cationic metallocene alkyl (or aryl or hydride) salt containing an inert, essentially non-coordinating anion. This form may be used alone or in conjunction with the hydrocarbylaluminoxane additives which increase the catalysts' activity and lifetimes. The cationic catalysts may be used as isolated solids or as catalyst liquors generated by the admixture of appropriate precursors, described below, without isolation of the catalyst salts.

Several classes of precursors are appropriate. The metallocene dialkyls (or diaryls or mixed aryl alkyls) described above may be treated with salts wherein the cation is a Brønsted-Lowry acid which is able to remove one alkyl group from the metal to generate alkane, the metal cation with inert anion, and a neutral, poorly coordinating base (e.g. tributylamine or N,N-dimethylaniline). Such precursors are known in the art and are extensively described, for example, in International Application No. PCT/US91/04390, Publication No. WO 92/00333, published Jan 9, 1992, whose teachings with respect thereto are incorporated herein by reference. A non-limiting example is given in equation 2 for clarification, where the anion A is described below, where Cp* represents $\eta$-$C_5(CH_3)_5$, Me is $CH_3$ and Ph is $C_6H_5$.

$$Cp^*_2MMe_2 + [Ph(ME)_2NH]^+[A]^- \rightarrow [Cp^*_2MMe]^+ \cdot [A]^- + CH_4 + PhNMe_2 \qquad 2.$$

A second general class of precursors are metallocene dialkyls and salts, wherein the cation is an oxidizing agent, such as ferrocenium, triphenylcarbenium, silver ion and the like. In this case, the oxidizer presumably serves to enerate a transient metallocene dialkyl radical cation which decays by loss of a alkyl radical to generate the catalyst cation salt. A non-limiting example is given for clarification in equation 3, where Fc represents ferrocene, $(\eta$-$C_5H_5)_2Fe$.

$$Cp^*_2MMe_2 + [Fc]^+[A]^- \rightarrow [Cp^*_2MMe]^+[A]^- + Fc(- + Me - Me, Me - H \text{ etc.}) \qquad 3.$$

The required qualities of the anion A are that it be inert toward reaction with the cationic catalyst, non-coordinating, bulky and unreactive toward the aluminum alkyl medium. Typical examples of A are $B(C_6F_5)_4$, $B[3,5\text{-}(CF_3)_2C_6H_4]_4$, $B(4\text{-}FC_6H_4)_4$; closo-carborane anions such as $CB_{11}H_{12}$ function as A as do closo-borane dianions such as $B_{10}H_{10}$ (forming salts of the type $M_2A$). Other anions can also be used as would be readily apparent to those skilled in the art in view of the above examples.

A third general method of generating the catalytically active cations is the abstraction of an alkyl group from the metallocene dialkyl by a powerful Lewis acid to produce the mono-alkyl cation and a anionic conjugate base which is inert to the medium and poorly coordinating. The catalyst liquor may be prepared without isolation of the salt (or Lewis acid/base adduct) which probably exists in solution as a dynamic equilibrium. A non-limiting example is shown in equation 4 for illustration.

$$Cp^*_2MMe_2 + B(C_6F_5)_3 \rightleftharpoons [Cp^*_2MME]^+ \cdot [MeB(C_6F_5)_3]^- \qquad 4.$$

Yet another useful type of catalyst is a neutral monoalkyl (or aryl or hydride) complex containing one cyclopentadienyl or substituted Cp ligand and one 6-electron donor dianionic ligand. Examples are the complexes $(\eta^5\text{-}C_5(Ch_3)_5)$ $(\eta^5\text{-}C_2B_9H_{11})MCH_3$, where the boron ligand is a nido-dicarbolide dianion.

Specific non-limiting examples of primary metallocenes which are useful in the invention include bis(cyclopentadienyl)zirconium dichloride, bis(cyclo-pentadienyl)hafnium dichloride, bis(pentamethylcyclopenta-dienyl)hafnium dichloride, bis(indenyl)hafnium dichloride, bis(methylcyclopentadienyl)hafnium dichloride, racemic and meso dimethylsilanyl bridged bis(methylcyclopentadienyl)hafnium dichloride, bis(cyclopentadienyl)titanium dichloride, bis(ethylcyclopentadienyl)zirconium dimethyl, bis($\beta$-phenyl-propylcyclopentadienyl)zirconium dimethyl, bis(methylcyclopentadienyl)zirconium dimethyl, racemic dimethylsilanyl bridged bis(indenyl)hafnium dichloride, racemic ethylene bridged bis(indenyl)zirconium dichloride, $(\eta^5\text{-}$indenyl)hafnium trichloride and $(\eta^5\text{-}C_5Me_5)$hafnium trichloride, and the like.

The aluminoxane co-catalysts are solutions or slurries in hydrocarbon solvent of oligomers of the general formula $(R''AlO)_y$, where R'' is methyl or a mixture of methyl with $C_2$ to about $C_{10}$ alkyl, and y is 5 to about 40, formed by partial hydrolysis of aluminum alkyls or mixtures of aluminum alkyls. Particularly effective are methyl aluminoxane (MAO, R''=methyl) and "modified" MAO (R''=methyl+octyl) prepared by partial co-hydrolysis of trimethyl-aluminum (TMA) and a long chain aluminum alkyl such as tri-n-octylaluminum (TNOA). When cationic alkyl complexes are used as catalysts, other aluminoxanes such as isobutyl aluminoxane (IBAO), produced from triisobutylaluminum (TIBA), are useful in enhancing catalytic activity.

The chain growth reaction may utilize a neat aluminum alkyl medium or may utilize up to about 90 wt percent of a hydrocarbon solvent diluent such as xylene, cumene, toluene, pentane, hexane, heptane, octane, decane, and the like. Reaction temperatures may vary from approximately room temperature (20° C.) to 150° C., with higher temperatures tending to increase olefinic and branched impurities. Pressures of ethylene may be varied from about 15 psig to 150 psig, with lower pressures tending to give higher $\beta$, smaller conversions (x) and less polyethylene.

The mole ratio of metallocene catalyst to aluminum alkyl may be varied from about $1 \times 10^{-7}$ to $1 \times 10^{-1}$ and preferably varies from about $1 \times 10^{-6}$ to $1 \times 10^{-2}$, and more preferably is in the range of $2 \times 10^{-3}$ to $5 \times 10^{-5}$. At most catalyst concentrations, the chain growth reaction can be mass-transport limited so that low stirring rates can be used to influence the product distribution, increasing $\beta$ and decreasing PE formation at the expense of conversion (x).

The mole ratio of aluminoxane to catalyst, expressed as moles of total aluminum in the aluminoxane, may range from about 5/1 at high catalyst concentration to 50,000/1 at low catalyst concentration. With some of the catalysts it is beneficial to add the aluminoxane either in portions throughout the reaction or continuously by means of a pump. This procedure minimizes the yield of PE and increases the conversion (x).

When conducting the chain growth reaction it is helpful to activate the catalyst in order to avoid an induction period. Two methods are convenient. In method 1, the catalyst is heated in the aluminum alkyl under ethylene for 10–20 minutes prior to addition of the aluminoxane co-catalyst, whereupon immediate ethylene uptake occurs. In method 2, the catalyst is incubated in aluminoxane solution in a separate vessel for about 5 minutes at 20° C.. Subsequent addition to the aluminum alkyl permits immediate uptake of ethylene.

The aluminum alkyl feed compounds for the chain growth include trialkyl aluminums and dialkyl aluminum hydrides which can be represented by the formula $R_mAlH_n$ where m is 2 or 3 and n is 0 or 1, m+n=3, and R is $C_1$ to $C_{20}$ alkyl which can be the same or different. Mixtures of these compounds can be used. Specific non-limiting examples of suitable feed compounds include triethylaluminum, tri-n-propylaluminum, tri-n-butylaluminum, tri-n-hexylaluminum, diethylaluminum hydride, and the like.

Preferred aluminum alkyl feed stocks for the chain growth process are low molecular weight aluminum alkyls having alkyl groups with even carbon numbers and especially triethylaluminum (TEA) and tri-n-butylaluminum (TNBA).

$C_6$ to $C_{20+}$ alpha olefins can be recovered from the alkylaluminum chain growth products by thermal or catalytic displacement by known procedures such as, for example, using ethylene and/or butene as the displacing olefin as described in U.S. Pat. No. 4,935,569. Alternatively, the chain growth products can be oxidized and hydrolyzed using known procedures to produce linear primary alcohols.

The invention is further illustrated by, but is not intended to be limited to, the following examples which are conducted according to the general procedures hereinafter described.

The manipulation of catalysts, aluminum alkyls, and aluminoxanes, the assembly and disassembly of reactors, and the initial filtration of polyethylene were conducted in a nitrogen filled glovebox. The addition of aluminoxanes to reactors was done by syringe under a nitrogen or ethylene flow, as described below. The aluminum alkyls triethylaluminum (TEA) and tri-n-butylaluminum (TNBA) used are commercial products of Ethyl Corporation as is methyl aluminoxane (MAO) which is provided as a solution in toluene. "Modified" MAO consists of the co-hydrolysis products of trimethylaluminum (TMA) and tri-n-octylaluminum (TNOA) in toluene. Ethylene was polymer grade, used without purification. Other solvents and reagents were dried and degassed by conventional methods. Preparation of catalysts was conducted by conventional methods described in the literature.

Quantitative analysis of aluminum alkyl reaction products was conducted as follows. While assembling the reactors, a known amount of n-undecane was added to the reaction mixture. After reaction completion, a small aliquot of the product in toluene was hydrolyzed with degassed aqueous HCl (20%). Analysis of the product hydrocarbons by gas chromatograph utilized a Hewlett-Packard 5890-II instrument, a model 3396-II integrator and a 50 m, 0.2 mm i.d. capillary column bonded with HP-1 phase. The data, moles of n-alkane vs p, were reiteratively fitted to the Schulz-Flory distribution to obtain best-fit values of $\beta$ and x.

Reactions were conducted in three types of apparatus. The first, designated Apparatus A, is a 6-oz Fischer-Porter pressure bottle connected with a O-ring and stainless steel adapter to a pressure head. This head consists of a stainless steel cross-tee fitted with a steel ball valve directly above the bottle. The cross-tee was fitted on one side-arm with a needle valve connected to ethylene and connected on the other side-arm to a steel tee fitted with a pressure gauge and with a pressure relief valve. This arrangement allows a syringe needle to deliver MAO or other liquids directly into the reaction bottle. The use of Apparatus A is described in Examples 1 and 2, below.

Apparatus B consists of a 300 mL Parr autoclave, constructed of stainless steel, modified as follows. One of the access valves on the autoclave was connected to ethylene/vacuum for evacuation and pressurization of the vessel's headspace. Another access valve was connected within the vessel to a shortened dip tube for MAO delivery. This valve was connected outside of the vessel, by means of a ⅛ in. diameter Teflon ® tube, to a stainless steel charging bomb. Atop this bomb was the pressure head described with respect to Apparatus A with the bomb in place of the Fischer-Porter bottle and with the needle valve connected to pressurized nitrogen. This arrangement allows MAO to be added in increments to the charging bomb by syringe and then trans-ferred by excess nitrogen pressure into the autoclave. The use of Apparatus B is described in Examples 12 and 15, below.

Apparatus C consists of the autoclave described as Apparatus B, above, where the charging bomb is replaced with a metering pump (Fluid Metering, Inc., Oyster Bay, NY), which delivers modified MAO as a constant rate. Thus MAO is pumped from a graduated reservoir at ambient pressure of argon into the pressurized autoclave through the Teflon ® tube and shortened dip tube. The use of Apparatus C is described in Example 16, below.

EXAMPLES 1-11

The reaction parameters and results of reactions conducted using Apparatus A are given in Table 1. Details of Examples 1 and 2 are given here to exemplify the procedures. The oligomer distribution and purity for these examples is shown in Table 4.

EXAMPLE 1

Into the Fischer-Porter bottle were weighed 34 mg (0.065 mmol) of $[\eta^5\text{-}C_5(CH_3)_5]_2HfCl_2$ and then 200 μL of n-undecane, 5.00 mL (36.6 mmol) of TEA and 5.00mL of toluene were added by syringe. Apparatus A was assembled, briefly evacuated through the ball valve and then pressurized to 50 psig with ethylene. The bottle was partially immersed in a 80° C. oil bath for 25 minutes to activate the catalyst. The ethylene pressure was then vented and 440 μL of MAO in toluene (3.88 wt % Al) was added by syringe. The bottle was repressurized with ethylene to 50 psig and heating was continued for 61 minutes with vigorous magnetic stirring. After venting and cooling, the apparatus was weighed and, by difference, 5.8 g of ethylene had reacted; PE was filtered out, washed with toluene and dried, weight 0.80 g. Hydrolysis of an aliquot of the filtrate and analysis as described above gave the values of x and β shown in Table 1 and the purities shown in Table 4. Catalyst activity for oligomerization was 2,800 mol $C_2H_4$/mol Hf/hour.

EXAMPLE 2

Into a Fischer-Porter bottle were weighd 35 mg (0.073 mmol) of $\eta^5$-indenyl)$_2$HfCl$_2$, and then 200 μL n-undecane, 5.00 mL (36.6 mmol) TEA and 5.00 mL of toluene were added. Apparatus A was assembled, briefly evacuated, pressurized with ethylene and partially immersed in a hot oil bath. The solution was heated at 80° C. for 20 minutes to activate the catalyst. The pressure was then vented and 400 μL of MAO (3.99 wt % Al) was added by syringe. The apparatus was repressurized with ethylene and heated for 60 minutes at 80° C., 100 psig with vigorous magnetic stirring, during which time 8.8 g of ethylene were consumed. The apparatus was vented and cooled, allowing PE to precipitate. The PE was filtered, washed with toluene, dried and weighed (2.8 g). An aliquot of the filtrate was diluted, hydrolyzed and analyzed as described above. Catalyst activity for oligomerization was 2,900 mol $C_2H_4$/mol Hf/hour.

TABLE 1

| Example | $R_3Al^1$ mmol | Catalyst$^2$ $R_3Al$/equiv | Activation$^3$ method | Pressure psig | Time Hours | MAO$^4$ equiv/cat | x | β | % PE$^5$ |
|---|---|---|---|---|---|---|---|---|---|
| 1 | TEA 36.6 | C 500 | 1 | 50 | 1.0 | 7.5 | 1.3 | 0.47 | 14 |
| 2 | TEA 36.6 | D 500 | 1 | 100 | 1.0 | 7.5 | 1.8 | 0.50 | 31 |
| 3 | TEA. neat 36.6 | A 5000 | 1 | 100 | 2.0 | 7.5 | 0.34 | 0.18 | nd |
| 4 | TNBA. neat 20.8 | A 5000 | 1 | 100 | 1.5 | 7.5 | 0.70 | 0.25 | nd |
| 5 | TEA 36.6 | A 500 | 1 | 100 | 1.0 | 7.5 | 1.0 | .20 | nd |
| 6 | TEA 36.6 | B 500 | 1 | 100 | 1.0 | 7.5 | 1.4 | 0.44 | 19 |
| 7 | TEA 36.6 | C 500 | 1 | 100 | 0.5 | 7.5 | 1.0 | 0.27 | nd |
| 8 | TEA 36.6 | E 500 | 1 | 100 | 1.0 | 7.5 | 1.0 | 0.37 | 26 |
| 9 | TEA 36.6 | F 500 | 1 | 100 | 1.0 | 15 1 part | 1.5 | 0.44 | 51 |
| 10 | TEA 36.6 | F 500 | 1 | 100 | 1.0 | 15 2 parts | 1.7 | 0.30 | 34 |
| 11 | TEA 36.6 | B 500 | 2 | 100 | 0.83 | 96 6 parts | 1.7 | 0.40 | 6 |

$^1$Conducted in 50% (v/v) TEA/toluene unless otherwise noted.
$^2$Catalysts used -
A. $(\eta^5\text{-}C_5H_5)_2HfCl_2$:
B. $(\eta^5\text{-}C_5H_4CH_3)_2HfCl_2$:
C. $[\eta^5\text{-}C_5(CH_3)_5]_2HfCl_2$:
D. $(\eta^5\text{-indenyl})_2HfCl_2$:
E. rac-ansa-$(CH_3)_2Si[\eta^5\text{-}C_5H_3CH_3)]HfCl_2$:
F. rac-ansa-$(CH_3)_2Si[\eta^5\text{-indenyl})_2HfCl_2$.
$^3$Method 1: catalyst incubated in hot TEA/$C_2H_4$.
Method 2: catalyst incubated in MAO.
$^4$MAO commercial sample in toluene added via syringe one initial portion, unless otherwise noted. When added in parts, the total equiv. noted was added in equal increments throughout the reaction.
$^5$Polyethylene % yield base on consumed ethylene;
nd = not determined.

EXAMPLES 12-15

The reaction parameters and results of reactions conducted using Apparatus B are given in Table 2. Details of Examples 12 and 15 are given here to exemplify the procedures.

EXAMPLE 12

Into the Parr autoclave were weighed 91 mg (0.22 mmol) of $(\eta^5\text{-}C_5H_4CH_3)_2HfCl_2$, and then 30.0 mL (219 mmol) of TEA and 1.00 ml of undecane were added. The nitrogen filled charging bomb was attached and the autoclave was briefly evacuated and then pressurized with ethylene to 100 psig. While heating the autoclave at 80° C. for 20 minutes with a stirring rate of 250 rpm, 2.0 ml of a toluene solution of "modified" MAO (8.3 wt. percent Al, $C_1$:$C_8$ ratio 4:1) was introduced into the charging bomb via syringe, and the bomb was pressurized to 110 psig with nitrogen. The MAO was transferred into the autoclave taking care to minimize contamination by nitrogen. Heating at 100 psig, 80° C. was continued for 85 minutes with five subsequent 2.0 ml additions of MAO. The autoclave was weighted and, by difference, 26.6 g of ethylene had reacted. Upon cooling, the precipitated PE was filtered, washed successively with toluene, methanol, 20% aqueous HCl, water and methanol and then dried to give 0.87 g of by-product. An aliquot of the reaction product was hydrolyzed and analyzed as described above to give the n-alkane distribution and purity shown in Table 4 and the values of x and β shown in Table 2. Catalyst activity for oligomerization was 3,000 mol $C_2H_4$/mol Hf/hour.

EXAMPLE 15

To the autoclave were added 9 mg (0.022 mmol) of $\eta^5$-$(C_5H_4Ch_3)_2HfCl_2$, 30.0 mL of TEA and 1.00 ml of undecane. This mixture was heated at 110° C., 100 psig of ethylene for 10 minutes and then 2.0 ml of MAO (7.2 wt. % Al, 4.7 mmol) was added from the charging bomb. The reaction temperature was increased and held at 120° C., 100 psig for 80 minutes during which time seven further 2.0 ml MAO additions were made. A total of 39 g of ethylene reacted. The polyethylene was collected as described in Example 12 and weighed 2.1 g. Product hydrolysis and analysis generated the data in Table 3 and the values of x and β reported in Table 2. Catalyst activity for oligomer formation was 45,000 mol $C_2H_4$/mol Hf/hour.

EXAMPLES 16-18

The reaction parameters and results of reactions conducted using Apparatus C are given in Table 3. Details of Example 16 are given here to exemplify the procedure.

EXAMPLE 16

To the autoclave were added 11 mg (0.027 mmol) of ($\eta^5$-indenyl)$HfCl_3$, 30.0 mL of TEA and 1.00 mL of undecane. This mixture was heated to 80° C., 90 psi of ethylene for 22 minutes then a solution of modified MAO in toluene (5.8 wt % aluminum) was added at a constant rate of 0.20 mL/min for 70 minutes with a stirring rate of 600 RPM. The pressure and temperature were maintained during this period, in which time 54 g of ethylene reacted. The polyethylene was collected as described in Example 12 and weighed 5.76 g. Product hydrolysis and analysis generated the data in Table 4 and the values of x and β reported in Table 3. Catalyst activity for oligomer formation was 64,000 mol $C_2H_4$/mol Hf/hour.

TABLE 2

| Examples | Catalyst[1] $R_3Al$/equiv | Stirring rate RPM | Temperature °C. | Time Hours | MAO[2] equiv/cat | x | β | % PE[3] |
|---|---|---|---|---|---|---|---|---|
| 12 | 1000 | 250 | 80 | 1.4 | 220 in 6 parts | 1.2 | 0.50 | 3 |
| 13 | 1000 | 600 | 80 | 1.4 | 320 in 9 parts | 1.5 | 0.30 | 20 |
| 14 | 10000 | 600 | 100 | 1.3 | 1270 in 6 parts | 1.4 | 0.30 | 13 |
| 15 | 10000 | 600 | 120 | 1.3 | 1700 in 8 parts | 1.5 | 0.42 | 6 |

[1]These reactions were conducted in neat TEA using ($\eta^5$-$C_5H_4CH_3)_2HfCl_2$ as catalyst.
[2]Toluene solutions of MAO were added incrementally with the charging bomb. Commercial MAO was used in Examples 14 and 15 while "modified" MAO was used in Examples 12 and 13.
[3]Polyethylene % yield based on consumed ethylene.

TABLE 3

| Example | $R_3Al$[1] | Catalyst $R_3Al$/equiv | Stir Rate RPM | Time Hours | Temp. °C. | x | β | % PE |
|---|---|---|---|---|---|---|---|---|
| 16 | TEA | 8000 | 600 | 1.2 | 80 | 2.3 | 0.40 | 10 |
| 17 | TNBA | 8000 | 600 | 1.0 | 80 | 1.2 | 0.29 | 32 |
| 18 | TNBA[2] | 5000 | 450 | 1.3 | 65 | 1.3 | 0.73 | 15 |

[1]Reactions were conducted in neat $R_3Al$ using ($\eta^5$-indenyl)$HfCl_3$ catalyst as described for Example 16 except as noted.
[2]($\eta^5$-indenyl)$_2HfCl_2$ catalyst.

TABLE 4

| | n-Alkane Distribution and Purity, mmol (Area %) | | | | |
|---|---|---|---|---|---|
| $C_n$ | Ex. 1 | Ex. 2 | Ex. 12 | Ex 15[1] | Ex. 16[2] |
| 6 | 10.6 (97.5) | 15.3 (97.3) | 49.3 (95.6) | 66.2 (91.8) | 80.5 (99.1) |
| 8 | 7.23 (97.8) | 9.63 (97.2) | 45.5 (98.2) | 47.3 (91.1) | 76.1 (99.7) |
| 10 | 4.96 (100) | 6.27 (95.7) | 26.3 (97.7) | 33.8 (89.6) | 54.1 (99.5) |
| 12 | 3.17 (99.2) | 4.04 (94.8) | 16.3 (95.7) | 22.4 (87.7) | 37.9 (99.6) |
| 14 | 2.16 (99.2) | 2.89 (93.2) | 10.6 (94.0) | 15.6 (85.5) | 27.3 (99.5) |
| 16 | 1.51 (99.2) | 2.15 (94.1) | 6.89 (93.3) | 11.0 (82.5) | 19.5 (99.2) |
| 18 | 1.09 (100) | 1.67 (93.4) | 4.61 (92.9) | 8.19 (81.4) | 14.0 (99.5) |
| 20 | 0.77 (100) | 1.29 (94.3) | 2.92 (92.6) | 5.51 (84.5) | 9.59 (99.3) |
| 22–30[3] | 1.80 | 3.88 | 5.00 | 11.5 | 20.4 |

[1]In Example 15 the principle impurities are α-olefins (about 5 area %) with lesser amounts of internal and/or branched olefins.
[2]In Example 16 the principle $C_6$ impurity is 1-hexene (0.9 area %)
[3]Total mmol.

What is claimed is:

1. In a process for the preparation of an aluminum alkyl chain growth product by the chain growth reaction of α-olefin on an aluminum alkyl, the improvement comprising catalyzing the chain growth reaction with a catalyst system which comprises at least oen of the following: (a) a metallocene of a transition metal and a methylaluminoxane, (b) a cationic transition metal metallocene complex with an inert non-coordinating anion and, (c) a cationic transition metl metallocene complex with an inert non-coordinating anion and a hydrocarbylaluminoxane.

2. The process of claim 1 wherein the α-olefin is ethylene.

3. The process of claim 1 wherein the aluminum alkyl is represented by the formula $R_mAlH_n$, where m is 2 or 3, n is 0 or 1, m+n=3 and R is $C_1$ to $C_{20}$ alkyl which can be the same or different.

4. The process of claim 3 wherein the aluminum alkyl is triethylaluminum.

5. The process of claim 3 wherein the aluminum alkyl is tri-n-butylaluminum

6. The process of claim 1 wherein the transition metal is a Group 4 metal.

7. The process of claim 6 wherein the Group 4 metal is zirconium or hafnium.

8. The process of claim 3 wherien the α-olefin is ethylene, the metallocene is represented by the formula $Z_t(\eta^5\text{-}R'_nH_mC_5)_8MX_{4-s}$ wherein R' is a carbon or carbon and heteroatom containing $C_1$ to $C_6$ alkyl, $C_3$ to $C_{12}$ cycloalkyl, or a $C_6$ to $C_{14}$ aryl substituent, two or more substituents can form cyclic groups fused to a cyclopentadienyl ring, and the R' groups can be different in type and number on each cyclopentadienyl ring, Z is a silane, phosphine, amine or carbon bridging group between two cyclopentadienyl rings, t is 0 or 1, m and n are integers of 0 to 5 and m+n=5 when t is 0 or 4 when t is 1, s is 1 or 2, M is a transition metal and X is halogen, pseudohalogen, hydride or alkyl and each X can be the same or different, the mole ratio of metallocene to aluminum alkyl is from about $1\times10^{-7}$ to $1\times10^{-1}$, the mole ratio of aluminoxane to metallocene is from about 5/1 to 50,000/1, the reaction temperature is from about 20° to 150° C. and the ethylene pressure is from about 15 to 150 psig.

9. The process of claim 8 wherein the transition metal is zirconium or hafnium.

10. In a process for the preparation of linear alpha-olefins by the chain growth reaction of α-olefin on an aluminum alkyl followed by olefin displacement of linear alpha-olefins from the aluminum alkyl chain growth product, the improvement comprisign catalyzing the chain growth reaction with a catalyst system which comprises at lease one of the following: (a) a metallocene of a transition metal and a methylaluminoxane, (b) a cationic transition metal metallocene complex with an inert non-coordinating anion and, (c) a cationic transition metal metallocene complex with an inert non-coordinating anion and a hydrocarbylaluminoxane.

11. The process of claim 10 wherien the α-olefin is ethylene.

12. The process of claim 10 wherein the aluminum alkyl is represented by the formula $R_mAlH_n$, where m is 2 or 3, n is 0 or 1, m+n=3 and R is $C_1$ to $C_{20}$ alkyl which can be the same or different.

13. The process of claim 10 wherein the aluminum alkyl is triethylaluminum.

14. The process of claim 10 wherein the aluminum alkyl is tri-n-butylaluminum.

15. The process of claim 10 wherein the transition metal is a Group 4 metal.

16. The process of claim 15 wherein the Group 4 metal is zirconium or hafnium.

17. The process of claim 12 wherien the α-olefin is ethylene, the metallocene is represented by the formula $Z_t(\eta^5\text{-}R'_nH_mC_5)_8MX_{4-s}$ wherein R' is a carbon or carbon and heteroatom containing $C_1$ to $C_6$ alkyl, $C_4$ to $C_8$ cycloalkyl, or a $C_6$ to $C_{10}$ aryl substituent, two or more substituents can form cyclic groups fused to a cyclopentadienyl ring, and the R' groups can be different in type and number on each cyclopentadienyl ring, Z is a silane, phosphine, amine or carbon bridging group between two cyclopentadienyl rings, t is 0 or 1, m and n are integers of 0 to 5 and m+n=5 when t is 0 or 4 when t is 1, s is 1 or 2, M is a transition metal and X is halogen, pseudohalogen, hydride or alkyl and each X can be the same or different, the mole ratio of metallocene to aluminum alkyl is from about $1\times10^{-7}$ to $1\times10^{-1}$, the mole ratio of aluminoxane to metallocene is from about 5/1 to 50,000/1, the reaction temperature is from about 20° to 150° C. and the ethylene pressure is from about 15 to 150 psig.

18. The process of claim 17 wherein the transition metal is zirconium or hafnium.

19. In a process for the preparation of linear primary alcohols by the chain growth reactions of α-olefin on an aluminum alkyl followed by oxidation of the aluminum alkyl chain growth product to form alkoxides and acid hydrolysis of the alkoxides to produce linear primary alcohols, the improvement comprising catalyzing the chain growth reaction with a catalyst system which comprises at lease one of the following: (a) a metallocene of a transition metal and a methylaluminoxane, (b) a cationic transition metal metallocene complex with an inert non-coordinating anion and, (c) a cationic transition metal metallocene complex with an inert non-coordinating anion and a hydrocarbylaluminoxane.

20. The process of claim 19 wherein the α-olefin is ethylene.

21. The process of claim 19 wherein the aluminum alkyl is represented by the formula $R_mAlH_n$, where m is 2 or 3, n is 0 or 1, m+n=3 and R is $C_1$ to $C_{20}$ alkyl which can be the same or different.

22. The process of claim 19 wherein the aluminum alkyl is triethylaluminum.

23. The process of claim 19 wherein the aluminum alkyl is tri-n-butylaluminum.

24. The process of claim 19 wherein the transition metal is a Group 4 metal.

25. The process of claim 24 wherein the Group 4 metal is zirconium or hafnium.

26. The process of claim 12 wherien the α-olefin is ethylene, the metallocene is represented by the formula $Z_t(\eta^5\text{-}R'_nH_mC_5)_8MX_{4-s}$ wherein R' is a carbon or carbon and heteroatom containing $C_1$ to $C_6$ alkyl, $C_4$ to $C_8$ cycloalkyl, or a $C_6$ to $C_{10}$ aryl substituent, two or more substituents can form cyclic groups fused to a cyclopentadienyl ring, and the R' groups can be different in type and number on each cyclopentadienyl ring, Z is a silane, phosphine, amine or carbon bridging group between two cyclopentadienyl rings, t is 0 or 1, m and n are integers of 0 to 5 and m+n=5 when t is 0 or 4 when t is 1, s is 1 or 2, M is a transition metal and X is halogen, pseudohalogen, hydride or alkyl and each X can be the same or different, the mole ratio of metallocene to aluminum alkyl is from about $1\times10^{-7}$ to $1\times10^{-1}$, the mole ratio of aluminoxane to metallocene is from about 5/1 to 50,000/1, the reaction temperature is from about 20° to 150° C. and the ethylene pressure is from about 15 to 150 psig and the transition metal is zirconium or hafnium.

* * * * *

UNITED STATES PATENT AND TRADEMARK OFFICE
CERTIFICATE OF CORRECTION

PATENT NO. : 5,210,338
DATED : May 11, 1993
INVENTOR(S) : EDWARD G. SAMSEL

It is certified that error appears in the above-indentified patent and that said Letters Patent is hereby corrected as shown below:

Column 11, line 5, reads: "...at least oen of..."
  but should read: -- ...at least one of... --

Column 11, line 41, reads: "...5/1 to 50.000/1..."
  but should read: -- ...5/1 to 50,000/1... --

Column 11, line 49, reads: "...improvement comprisign..."
  but should read: -- ...improvement comprising... --

Column 12, line 49, reads: "...of claim 12 wherien..."
  but should read: -- ...of claim 21 wherein... --

Signed and Sealed this

Fifteenth Day of February, 1994

Attest:

BRUCE LEHMAN

*Attesting Officer*     *Commissioner of Patents and Trademarks*